(12) United States Patent
Gorritxategi et al.

(10) Patent No.: US 9,063,075 B2
(45) Date of Patent: Jun. 23, 2015

(54) METHOD AND DEVICE FOR DETERMINING THE STATE OF DEGRADATION OF A LUBRICANT OIL

(75) Inventors: Eneko Arrondo Gorritxategi, Guipúzcoa (ES); Aitor Arnaiz Irigaray, Guipúzcoa (ES); Ana Aranzabe Garcia, Guipúzcoa (ES); Jesús Ma Terradillos Azqueta, Guipúzcoa (ES)

(73) Assignee: FUNDACION TEKNIKER, Eibar, Guipuzcoa (ES)

( * ) Notice: Subject to any disclaimer, the term of this patent is extended or adjusted under 35 U.S.C. 154(b) by 191 days.

(21) Appl. No.: 13/820,274

(22) PCT Filed: Sep. 7, 2010

(86) PCT No.: PCT/ES2010/070582
§ 371 (c)(1),
(2), (4) Date: Mar. 20, 2013

(87) PCT Pub. No.: WO2012/032197
PCT Pub. Date: Mar. 15, 2012

(65) Prior Publication Data
US 2014/0146307 A1    May 29, 2014

(51) Int. Cl.
*G01N 33/28* (2006.01)
*G01N 21/31* (2006.01)
*G01N 21/25* (2006.01)

(52) U.S. Cl.
CPC ............... *G01N 21/31* (2013.01); *G01N 21/25* (2013.01); *G01N 33/2888* (2013.01)

(58) Field of Classification Search
None
See application file for complete search history.

(56) References Cited

U.S. PATENT DOCUMENTS

| 5,194,910 A | 3/1993 | Kirkpatrick, Jr. et al. |
| 7,612,874 B2 | 11/2009 | Kong et al. |
| 2008/0024761 A1 | 1/2008 | Kong et al. |

FOREIGN PATENT DOCUMENTS

RU    2329502    7/2008

OTHER PUBLICATIONS

International Search Report (w/ English translation), PCT/ES2010/070582, completion date: Feb. 15, 2011; 4 pages.

*Primary Examiner* — Kara E Geisel
*Assistant Examiner* — Amanda Merlino

(57) ABSTRACT

The present invention provides a method and a device for determining the degradation of a used oil. The method of the invention is based on calculating the components in the red, green and blue transmission spectral bands $I_{Ro}$, $I_{Go}$ and $I_{Bo}$ of the unused oil, carrying out a number of measurements of the transmittance of the same oil after use, calculating the colour indices of the used oil and the reference colour index as $CI = 1 \times I_R + 0.5 \times I_G + 0.5 I_B$ $CI_{REF} = 1 \times I_{Ro} 0.5 \times I_{Go} + 0.5 I_{Bo}$ and obtaining the overall degradation value as $OD(\%) = 100 - 100 \times \log_{10}(CI_{REF}/CI)$. By virtue of the method and the corresponding device, real-time monitoring of oil degradation is facilitated.

3 Claims, 3 Drawing Sheets

METHOD AND DEVICE FOR DETERMINING THE STATE OF DEGRADATION OF A LUBRICANT OIL

FIELD OF THE INVENTION

The present invention relates to a method to determine the state of degradation of lubricant and hydraulic oil. More precisely, it relates to a method and device to provide an accurate reading of the total degradation throughout the use of oil by measuring the transmittance in the visible range of the color spectrum of said oil.

BACKGROUND OF THE INVENTION

The need for using appropriate sensors to carry out industrial oil monitoring has been acknowledge as a critical area by operating engineers, machinery manufacturers and even standard regulation organizations, especially during the last years, wherein the reliability, efficiency and safety on processes and/or products plays a very important role.

Industrial machinery, either energy generating motors or compressors, multipliers, etc. undergoes a lot of stops and failures due to degradation of lubricant and hydraulic oils. This issue causes risky situations when these machines are used as a component of more complex systems, so that the consequence of a stop in these cases is even worst, both from a point of view of cost and machine safety.

The reduction in useful lifetime of the equipment frequently causes unnecessary maintenance costs and current "off-line" measurement methodologies do not provide an early enough detection of the degradation process. Besides, in many environments (transportation, industrial, energy . . . ) this control methodology implies a significant logistic and economic burden for a very small environment. In order to face this issue, a new generation of sensors, capable of carrying out the analysis of the machine in real time, is being developed.

Taking all of the above into account, the use of intelligent sensors will allow in the medium term the optimization of useful lifetime, reducing costs and issues in the machinery. Critical machinery can benefit from an increase in reliability and the operating staff can take advantage of a load reduction in inadequate maintenance work.

The oil degradation process follows several well-known steps: first it undergoes a loss of additives content to later generate acid compounds. The percentage of acid constituents (as additives in the case of new lubricants and as oxidation compounds in the case of operating lubricants) is determined through analytic techniques. There are on-line measuring equipment as the one described in patent JP 2000146696 that use absorbency in the visible range of the electromagnetic spectrum to correlate it with the AN parameter. These methods have the limitation of only contemplating the oxidative degradation of oil, even though AN is one of the most indicative parameters of the lubricant oil state. Besides, this equipment cannot be used in motors due to the carbon generated during the combustion process. Carbon darkens oil, so that the change in color is not due to a change in the state of degradation of oil.

U.S. Pat. No. 7,612,874 introduces a method and device for monitoring oil deterioration in real time. This patent is based in calculating the deterioration by the chromatic ratio Cr=Ur/Ug (absorbency in red and green), to determine the thermic and oxidative deterioration of oil. The method, however, does not allow knowing the remaining life of oil.

U.S. Pat. No. 6,061,139 introduces a method and device for monitoring the thermic degradation of lubricants. This method uses the 850 nm band of light spectrum to determine the state of the oil. The use of a single band causes not having a high sensitivity and the result being affected by other factors.

Patent RU2329502 also uses measurements of the visible light spectrum transmittance with the 3 spectral ranges (red, green and blue) to result in the content of "total impurities", particles that are generated during oil degradation.

OBJECT OF THE INVENTION

The object of the present invention is to facilitate monitoring in real time and to provide a fast and reliable device and method for determining the state of degradation of oil that solves the aforementioned issues. The method and sensor offer as a result the oil degradation index (Oil Degradation, OD) which indicates the total degradation percentage at the monitoring or measurement time. The process comprises the following steps:

a. calculating the components in the red, green and blue bands of the spectrum of the unused oil transmittance, $I_{R0}$, $I_{G0}$ and $I_{B0}$ b. performing several measurements of the transmittance of the same oil already used in three bands and obtaining the arithmetic mean $I_R$, $I_G$ and $I_B$ c. calculating the color indexes of the used oil and the reference color index as $$CI = 1*I_R + 0.5*I_G + 0.5*I_B$$

$$CI_{REF} = 1*I_{R0} + 0.5*I_{G0} + 0.5*I_{B0}$$

d. obtaining the total degradation value as OD(%)=100−100*$LOG_{10}$ ($CI_{REF}$/CI). The corresponding device comprises a strong white light, a fluidic cell adapted for the passage of oil through it, a detector capable of transforming the amount of light emitted by the source and absorbed by the oil into an electric signal of the transmittance in the visible and programming means to carry out the aforementioned process. Optionally, it also comprises a particle filter and means for eliminating bubbles in oil.

BRIEF DESCRIPTION OF THE DRAWINGS

In order to help better understand the present description, according to a preferred embodiment of the invention, a set of drawings is attached as way of illustration but not limited to.

DETAILED DESCRIPTION OF THE INVENTION

Figure 1:
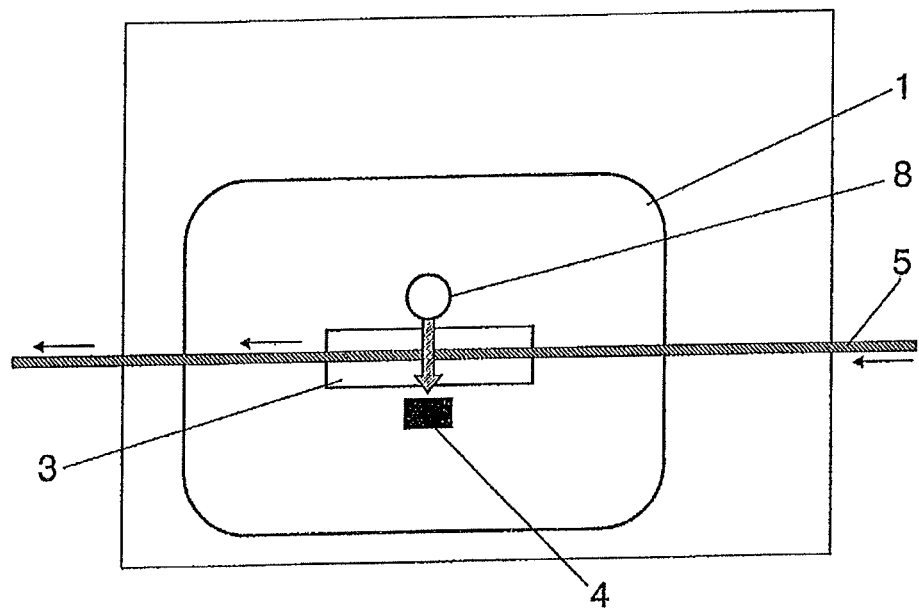
FIG. 1: is a diagram of the measurement principle, where the intensity of light transmitted after its passage through the oil and collected by the detector is represented.
Figure 2:
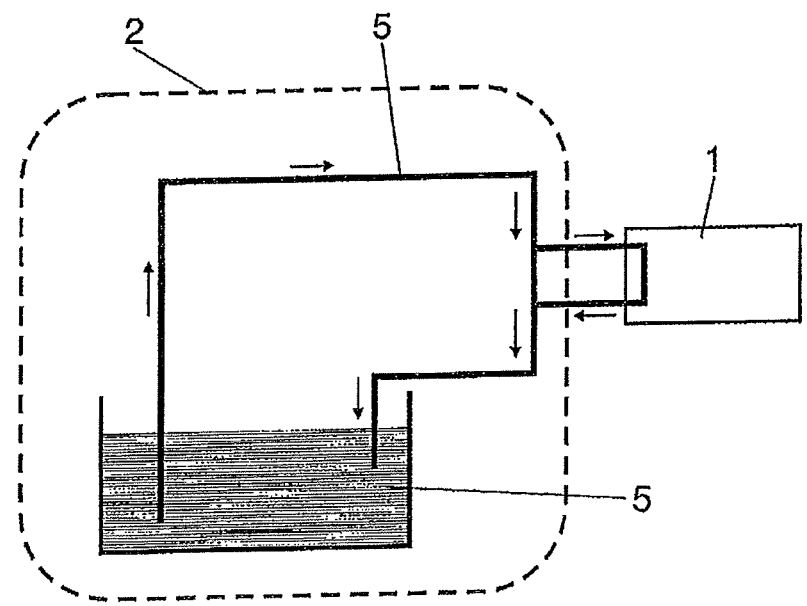
FIG. 2: is a diagram of the implementation of the sensor of the invention in a lubricating system.

Referring to FIGS. 1 and 2, the sensor of the invention (1) is devised to be installed in a by-pass of the lubrication system (2). The system takes advantage of the difference in pressure needed for the oil (5) to circulate through the sensor. The oil, after by-pass, goes through a series of hydraulic components inside the sensor: an electrovalve that manages the passage of oil through the device, a particle filter to eliminate particles of a certain size, and a system to eliminate bubbles that are generated in the oil's circulation system. After going through all the hydraulic elements, the oil goes to the fluidic cell (3) where the measurement will take place. This cell has an established light passage. With the oil already inside the cell, a white light beam is placed on the visible range of the spectrum through a LED-type emitter (8) and the light that is not absorbed by the oil is collected by a detector (i.e. a photodiode). The detector (4) collects the light in several wave lengths of the visible spectrum. Said spectrum range covers wave lengths ranging between 380 nm and 780 nm. For measurements in the visible transmission spectroscopy is used. A visible light beam goes through the oil inside the glass fluidic cell. The light intensity transmitted is given by Lambert-Beer law:

$$I(x)=I_0 e-Kx$$

K: Absorption Constant

The technique used in the sensors of the state of the art to monitor used oil degradation is based on the search for information in the visible spectrum, correlating the physic-chemical variables of the lubricant oil (Acid Number AN, Viscosity . . . ) with the change in color of the sample. The degradation index calculated by known methods is a mix of several laboratory parameters related to the determination of the oil degradation state. These parameters are RUL (Remaining useful lifetime) Oxidation (FTIR Fourier Transform Infrared), Acid Number (AN) and Viscosity. Each parameter is indicative of a certain degree of degradation, i.e. RUL is indicative of the beginning of the degradation process, when the additives are being consumed. AN and Oxidation by FTIR are indicative later, when the first acid compounds are being generated. In some cases, the AN is also a good indicator that additives are being lost, since its value varies (decreases) to later increase. Viscosity is the last to vary, almost at the end of the useful lifetime of the oil. The darkening or color change in oil however, is shown from beginning to end, from the moment the additives are being consumed until it is completely degraded. The transmittance percentage varies as the oil is being degraded. Correlating all these parameters to calculate the degradation state is however more time consuming than applying the method of the invention.

Lubricant oils can have different colors at first. Elements responsible for color in a lubricant oil are the base oil and the additives.

Base oil: Lubricant color varies depending on the refining degree and the source of the refined oil.

Additives: Some additives determine color in the final oil. In particular, those additives containing sulfur in their composition have more influence in the final color thereof (like for example some detergent or antioxidant additives).

Lubricants darken with use. A color change in lubricants indicates some kind of contamination, overheating, excessive degradation or an inappropriate lubricant.

The remaining useful lifetime calculation method according to the invention takes into account the components in the red, green and blue bands of the unused oil transmittance (referenced or new) $I_{RO}, I_{GO}$ and $I_{BO}$.

Optionally, in order to reduce noise in the signal, a measurement in dark (with no light on the detector) is performed in order to subtract it from the subsequent measurements. Next, several measurements of the transmittance (preferably 50) are performed and an arithmetic measurement of the transmittance for each color is obtained, with which values $I_R, I_G$ and $I_B$ are obtained (transmittance in the three main bands for used oil). Through these values, the color index value of the oil measured by the formula and the value of the reference oil are obtained.

$$CI=1*I_R+0.5*I_G+0.5I_B$$

$$CI_{REF}=1*I_{R0}+0.5*I_{G0}+0.5I_{B0}$$

Through the color index of the used oil and the reference oil, the oil degradation value (Oil Degradation, OD) is obtained and is calculated by:

$$OD(\%)=100-100*LOG_{10}(CI_{REF}/CI)$$

Each user will set the degradation limits to his liking but the oil is considered to be exhausted when the OD value reaches cero. Also, alarms can be applied to 10%, 20% or 30% levels so the progression of oil can be monitored.

Figure 3A:
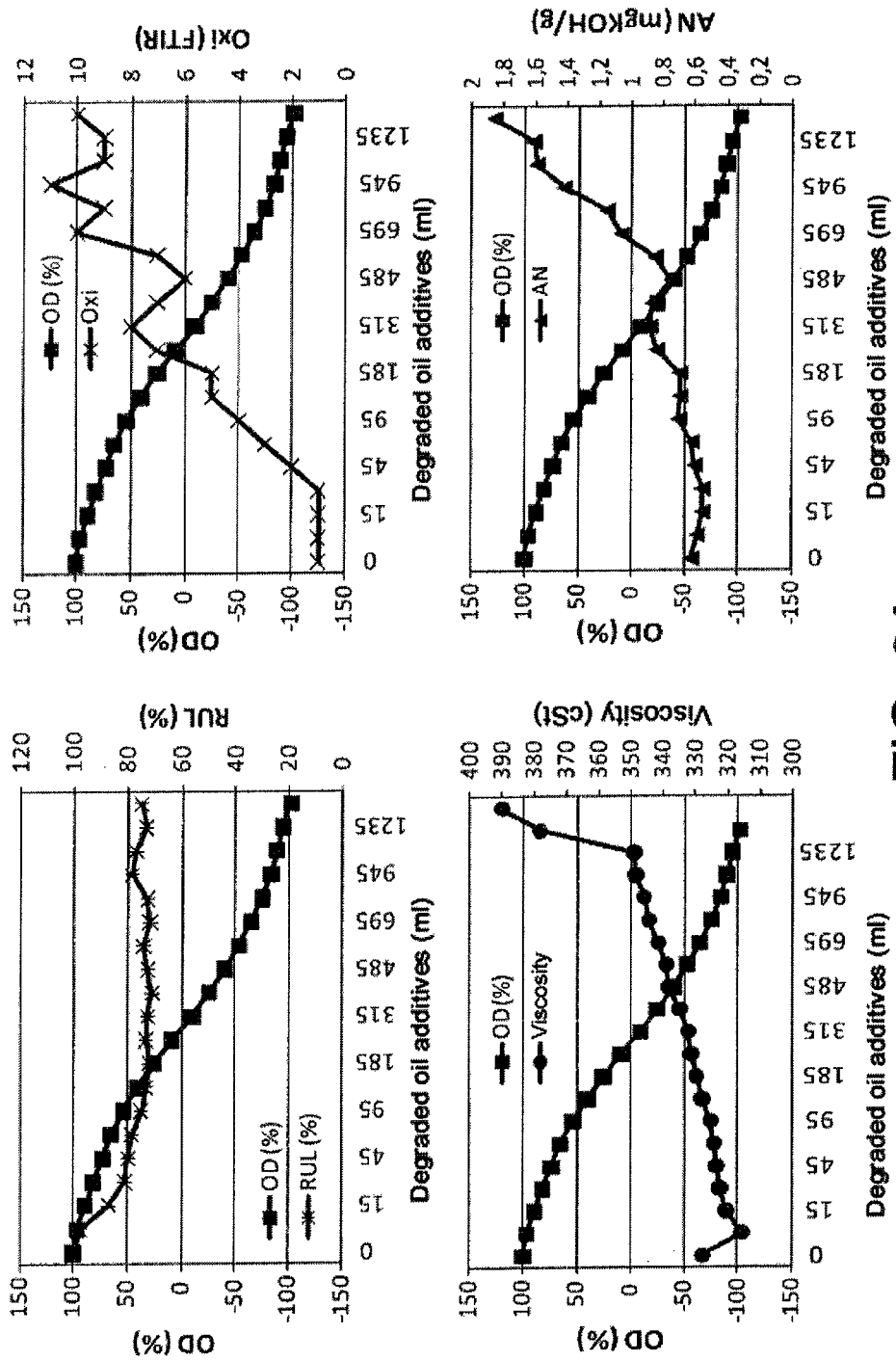
FIGS. 3a and 3b: are graphics where the oil degradation (OD) value measured according to the invention is represented in comparison with the most representative parameters of the degradation of two different oils.
Figure 3B:
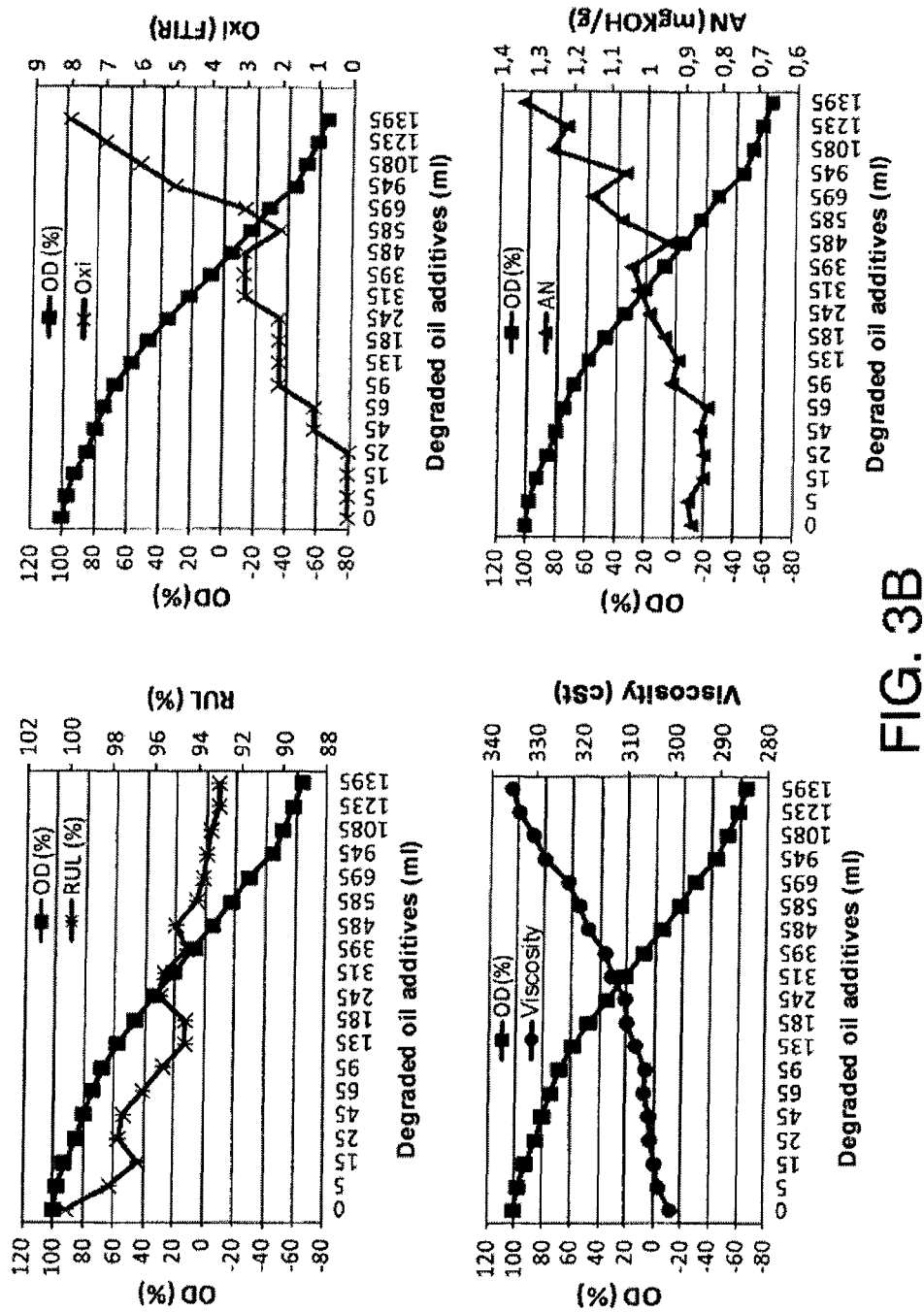

FIGS. 3a and 3b show tests performed on two types of oil: Fuch Renolyn 320© and Shell Omala HD 320©. Test was performed through the above mentioned method and different degrees of degradation were obtained until achieving the complete degradation of the oil tested. The degradation index OD was obtained and the laboratory parameters compared through the sensor of the invention.

FIG. 3 represents the results from the Fuch Renolyn 320 oil degradation process in which the OD (%) degradation index results are compared to the different laboratory parameters; RUL, AN, Oxi by FTIR and Viscosity. The RUL graphic shows that the RUL variation occurs in the first stage of the degradation process, while the additives are being exhausted.

Oxidation (Oxi) is the second parameter to start varying and next is the AN. Viscosity shows changes in advanced degradation states.

FIGS. 3A and 3B show how the value offered by the sensor of the invention optimally identifies oil degradation, since the OD parameter behaves in a very stable way during the whole oil degradation process, unlike other parameters. A direct relationship between the degradation index OD and the RUL in the first stage of the process is observed. An inverse relationship with the rest of the parameters is also identified. In this case, it can be seen that the viscosity varies during the whole degradation and parameters Oxi (FTIR) and AN start varying later.

The invention claimed is:

1. Process for calculating the total degradation of used lubricant oil comprising the following steps:
   a. calculating the components in the red, green and blue bands of the spectrum of the unused oil transmittance, $I_{RO}, I_{GO}$ and $I_{BO}$
   b. performing several measurements of the transmittance of the same oil already used in three bands and obtaining the arithmetic mean $I_R, I_G$ and $I_B$;
   c. calculating the color indexes of the used oil and the reference color index as $$CI=1*I_R+0.5*I_B+0.5 I_B$$

$$CI_{REF}=1*I_{RO}+0.5*I_{BO}+0.5 I_{BO}$$

d. obtaining the total degradation value as $OD(\%)=100-100*LOG_{10}(CI_{REF}/CI)$.

2. The process for determining the state of degradation of a used lubricant oil of claim 1, comprising a white light beam (8), a fluidic cell (3) adapted for the passage of oil through it, a detector (4) capable of transforming the amount of light emitted by the source and absorbed by the oil into an electric signal characteristic of the transmittance.

3. The processing according to claim 2 further comprising a particle filter and means to eliminate bubbles in oil.

* * * * *